United States Patent [19]

Fima

[11] Patent Number: 5,111,055
[45] Date of Patent: May 5, 1992

[54] METHOD AND SYSTEM FOR THE OPTICAL MEASUREMENT OF THE AIR PRESSURE BY LASER EXCITATION, PARTICULARLY IN FRONT OF AN AIRCRAFT

[75] Inventor: Henri Fima, Malissard, France

[73] Assignee: Sextant Avionique, Valence, France

[21] Appl. No.: 655,915

[22] Filed: Feb. 15, 1991

[30] Foreign Application Priority Data

Feb. 22, 1990 [FR] France .................. 90 02181

[51] Int. Cl.⁵ .................. G01L 11/00; G01N 21/64
[52] U.S. Cl. .................. 250/461.1; 250/459.1
[58] Field of Search .......... 250/461.1, 459.1, 458.1; 73/705

[56] References Cited

U.S. PATENT DOCUMENTS

| | | | |
|---|---|---|---|
| 4,493,553 | 1/1985 | Korb et al. ........... | 356/43 |
| 4,591,721 | 5/1986 | Wong ................... | 250/373 |

FOREIGN PATENT DOCUMENTS

| | | |
|---|---|---|
| 2508639 | 6/1981 | France . |
| WO86/02445 | 4/1986 | PCT Int'l Appl. . |

OTHER PUBLICATIONS

Optics Letters, "Proposed Single-Pulse Two-Dimensional Temperature and Density Measurements of Oxygen and Air", vol. 13, No. 3, Mar. 1988.

Review of Scientific Instruments, "A Lidar System for Measuring Atmospheric Pressure and Temperature Profiles", vol. 58, No. 12, Dec. 1987.

Primary Examiner—Edward P. Westin
Assistant Examiner—Richard Hanig
Attorney, Agent, or Firm—Lowe, Price, LeBlanc & Becker

[57] ABSTRACT

A method is disclosed for the optical remote measurement of the pressure of the air at a distance by laser excitation in which backscattered radiation is caused by means of a laser generator with very fine spectral line and by excitation of an absorption spectral line of molecular oxygen, the backscattered energies are measured at two different distances, the ratio of these energies is determined, a coefficient of absorption is derived therefrom depending on the temperature and the molecular density of oxygen and the density and so the pressure are calculated. An absorption spectral line is excited belonging to a Schumann-Runge band of molecular oxygen and the absorption spectral line is very wide with respect to the Rayleigh diffusion spectrum.

14 Claims, 3 Drawing Sheets

METHOD AND SYSTEM FOR THE OPTICAL MEASUREMENT OF THE AIR PRESSURE BY LASER EXCITATION, PARTICULARLY IN FRONT OF AN AIRCRAFT

BACKGROUND OF THE INVENTION

1. Field of the Invention

The present invention relates to a method and system for the optical remote measurement of the air pressure by laser excitation, particularly in front of an aircraft, in a zone undisturbed by its movement.

The air pressure is one of the parameters which are used, for controlling and piloting the aircraft, to elaborate then display certain parameters of the aircraft, such for example as its air speed, the mach number, its ground speed, its altitude, its power setting.

A conventional anemometer, called dynamic airspeed indicator, for example comprises static pressure intakes and a Pitot tube for total pressure intake. But the measurement of a dynamic airspeed indicator suffers from errors due to aerodynamic disturbances caused by the movement of the aircraft. It was then a priori interesting to invent an optical pressure measurement eliminating the drawbacks of conventional barometry, in order to obtain the true pressure of the ambient air.

2. Description of the Prior Art

From the document US-A-4 493 553 a method is already known for the optical remote measurement of the air pressure by laser excitation in which, having determined the air temperature, by means of a laser generator with very fine spectral line and by excitation of an absorption spectral line of molecular oxygen, backscattered radiation is caused, the backscattered energies are measured at two different distances, the ratio of these energies is determined, a coefficient of absorption is derived therefrom depending on the temperature and the molecular density of oxygen and the density and so the pressure is calculated.

But the spectral distribution of the outward and inward radiation is not the same, so that the coefficient of attenuation emitted radiation and the coefficient of attenuation of the backscattered radiation may not be the same. The pressure measurement would then be erroneous.

Also forming part of the state of the art is the article :"Proposed single pulse two dimensional temperature and density measurements of oxygen and air, Miler et al., March 1988, vol 13, no. 3, Optics Letters". This document teaches the use of an ArF laser tuned to a UV transition of oxygen while simultaneously observing the fluorescence and Rayleigh diffusion. For low absorption, the intensity of the Rayleigh backscatter is proportional to the molecular density and independent of the temperature in the tuning band of the ArF laser, as long as the temperature is less than 500 K. The Rayleigh diffusion makes it possible to obtain a spatial image of the density. To obtain the absolute value of the density, calibration is necessary. This measurement method consequently has limits.

SUMMARY OF THE INVENTION

An object of the present invention is first of all to provide a method for the optical remote measurement of the air pressure and which is fully satisfactory.

For this, the present invention provides a method for the optical remote measurement of the pressure of the air at a distance by laser excitation in which, having determined the air temperature, backscattered radiation is caused by means of a laser generator with very fine spectral line and by excitation of an absorption spectral line of molecular oxygen, the backscattered energies are measured at two different distances, the ratio of these energies is determined, a coefficient of absorption is derived therefrom depending on the temperature and the molecular density of oxygen and the density and so the pressure are calculated, characterized by the fact that an absorption spectral line is excited belonging to a Schumann-Runge band of molecular oxygen and the absorption spectral line is very wide with respect to the Rayleigh diffusion spectrum.

Advantageously, the laser generator emits two successive emission spectral lines which are very fine with respect to the absorption spectral line and are offset in frequency, one of the laser emission spectral lines is inside the absorption spectral line, the other outside, to determine the temperature, an optical measurement is made at a distance and, by means of the laser generator, two absorption spectral lines are excited which at least overlap and which belong respectively to two different Schumann-Runge bands of molecular oxygen, the emission spectral line of the laser generator has a very small width with respect to that of the absorption spectral lines and its central frequency is adjusted to be close to the maxima of the two absorption spectral lines, fluorescence of the oxygen is caused, the intensities of fluorescence induced in two different bands are measured, the ratio of these intensities is determined and the temperature derived therefrom.

Preferably, the temperature and pressure of the air are determined in front of an aircraft in a slice of air free of aerodynamic disturbances and flight parameters of the aircraft are derived therefrom which are used for piloting the aircraft.

The present invention also relates to a measurement system for implementing the measurement method of the invention, comprising a laser generator emitting a very fine spectral line radiation, an optical system for emitting the excitation radiation, an optical system for receiving the fluorescence and backscattered radiation, means for separating the backscattered radiation and the fluorescence radiation, a detector receiving the backscattered radiation, means for separating the two fluorescence energies, detectors tuned respectively to the fluorescence frequencies and a processing and computing module.

BRIEF DESCRIPTION OF THE DRAWINGS

The invention will be better understood from the following description of the theoretical principles on which the invention is based, the preferred implementation of the invention as well as the preferred embodiment of the system of the invention, with reference to the accompanying drawings in which.

DESCRIPTION OF THE PREFERRED EMBODIMENT

The overall energy of a molecule is the sum of its electron energy, its vibratory energy and its rotatory energy. This overall energy, from a fundamental electronic state, of lower energy, may occupy a series of different excited levels. With each each fundamental and excited electronic energy level are associated several near-by levels of vibratory energy with each of which are associated several even closer levels of rotatory energy corresponding to several values of the quantal rotation number J. The electronic and vibratory energy of a molecule passes to an upper level, particularly under excitation, i.e. by absorption of photons, coming for example from laser radiation. The electronic and vibratory energy of a molecule passes to a lower level, particularly by fluorescence, i.e. by spontaneous emission of photons.

Two distinct vibratory levels $E_i$ and $E_j$ of electronic and vibratory energy define an absorption or fluorescence band, grouping together the whole of the possible transitions between two rotatory energy levels associated respectively with these two electronic and vibratory energy levels. To a transition $E_i(J_k)$, $E_j(J_l)$ there corresponds a spectral line, theoretically of a given frequency, $$v = \frac{E_j(J_l) - E_i(J_k)}{h}$$

h being Planck's constant.

In actual fact, because of the thermal agitation (Doppler effect) and collisions, a spectral line, a curve representative of the absorption coefficient $\alpha$ as a function of the pulsation $\omega = 2\pi v$, is widened in frequency (pulsation).

The air pressure p, according to the law of perfect gases, is expressed by the relation:

$$p = N_A \frac{1}{1-q} kT$$

in which $N_A$ is the molecular density of dry air,

Q is the volume concentration of water vapor,

K is Boltzmann's constant,

T is the temperature.

In dry air, the oxygen mixture ratio is constant and equal to 20.95%, $N_0$ being the oxygen molecular density $$N_A = \frac{N_0}{0.2095}$$

Consequently, if Q and T are known, determination of $N_0$ makes it possible to calculate p.

DIFFERENTIAL ABSORPTION MEASUREMENT OF A LASER BEAM

The principle of the measurement consists in calculating the absorption coefficient $\alpha(\omega)$ in the central region of a molecular absorption spectral line of oxygen by finding the ratio of the backscattered energies, at two different distances, coming from a laser pulse of very fine spectral width with respect to the spectral line considered.

Since the coefficient $\alpha$ is a function of the molecular oxygen density and of the temperature, if we know the temperature, the measurement of $\alpha$ makes it possible to calculate the density and so the pressure.

But for that, the assumption must be verified according to which the attenuation coefficient for the radiation emitted, on the one hand, and for the backscattered radiation, on the other, is the same, i.e. that the factor of attenuation over a distance D travelled over twice, outward and inward, is equal to $e^{-2\alpha D}$. Now this assumption is not generally verified, for the spectral radiation distribution is not the same outward and inward The backscattered radiation comes essentially from aerosols and from molecular Rayleigh diffusion.

Figure 6:
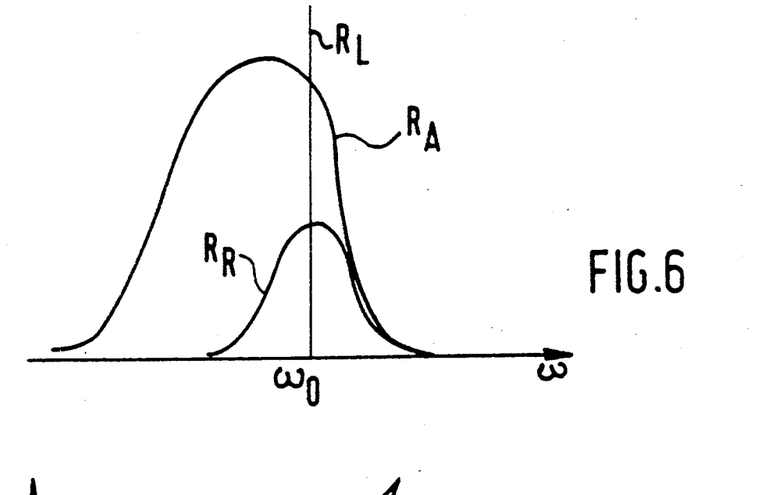
FIG. 6 is a representation of the prior art absorption and backscatter spectra with the laser spectral line.

Let us admit that the laser spectral line $R_L$ is practically monochromatic, $\omega_o$, at the scale of the absorption spectral line $R_A$ (FIG. 6). Aerosols have a very low agitation rate so that their backscattered spectrum, in a reference system immobile with respect to the air, is also monochromatic, with pulsation $\omega_o$. As for the backscatter spectrum $R_R$ of the molecules, because of the Doppler effect of the thermal agitation, it is very much widened. It is easy to see that, for example in the case of band A of oxygen centered at a wavelength of 0.76 μm, the overall width of an absorption spectral line at low altitude may vary between 2.5 and five times the Doppler width and that, from an altitude of 15 km, the width of the absorption spectral line is little greater than the Doppler width. The width of an absorption spectral line is at most equal to 2.5 times the width of the Rayleigh diffusion spectrum and becomes even twice smaller at a high altitude. The mean attenuation of the backscatter over a distance D is therefore not equal to $-\alpha_e(\omega_o)D$ but to a weighted mean of the relative intensities of the diffusion of the aerosols and the molecules. Such attenuation depends on parameters which are variable in space and calculation of the overall attenuation on the inward path, if all the backscatter spectrum is received, is impossible. The radiation received must be filtered through a spectral band centered on the frequency of the laser and very narrow with respect to the absorption spectral line. That is possible, by coherent detection, but it is particularly difficult.

In order, in practice, to use an absorption differential measurement of a laser beam, it is then necessary to find absorption spectral lines which are very wide with respect to the Rayleigh diffusion spectrum.

Let us consider the Schumann-Runge bands of diatomic molecular oxygen. They have in this case interesting features (Atlas of the Schumann-Runge $O_2$ absorption bands in the wavelength region 175-205 nm, Yoshino et al. J.Phys. Chem. Ref. Data, vol 13, no. 1, 1984).

These bands group together the transitions from the fundamental electronic state $$^3\Sigma^-_g,$$

referenced X, to the excited electronic state $$^3\Sigma^-_u,$$

referenced B.

The excitation frequency corresponding to the transition between the two original levels, respectively rest and excitation levels, with zero vibratory energy (fundamental vibratory state), is equal to 49 357 cm$^{-1}$, corresponding to a wavelength of 203 nm. The spectrum of the Schumann-Runge bands extends, in its discrete part, over the whole ultraviolet range, as far as the minimum wavelength of 175 nm. In this zone, there exists the argon-fluorine (ArF) excimer laser, tunable in the 192.8 nm −193.6 nm wavelength band. Beyond, the Schumann-Runge continuum extends with a high effective absorption section $\alpha/N_o$ (the dimension of $\alpha/N_o$ is m$^2$ since the dimension of $\alpha$, inverse of the wavelength, is m$^{-1}$ and that of $N_o$ is m$^{-3}$).

Widening of the spectral lines of the Schumann-Runge bands is in fact due to a phenomenon which dominates not only the Doppler effect but also molecular collisions. It is a question of the pre-dissociation of the molecules of the excited state B attributed to coupling with another repellent electronic state. The pre-dissociation probability, Q per unit of time, is very high and it is independent of the temperature and the pressure. Q in fact depends on the quantal numbers defining the energy level.

In the case of Schumann-Runge bands, the absorption spectral lines are very wide with respect to the Rayleigh diffusion spectrum and the above mentioned assumption is verified, the attenuation factor is equal to $$e^{-2\alpha D}$$

measurement of the attenuation then gives $$\alpha = N_o S(T) g(\omega)$$

in which relation S(T) is the intensity of the spectral line and g($\omega$) the standardized profile of the spectral line such that $$\int \alpha d\omega = N_o S(T)$$

In the case of Schumann-Runge bands, because of the preponderance of the pre-dissociation, g($\omega$) depends practically neither on the temperature nor on the pressure-density.

Knowing the temperature T, the measurement of $\alpha$ gives then $N_o$ and consequently the pressure p.

MEASUREMENT WITH TWO LASER SPECTRAL LINES

In actual fact, for the above described differential method to be applicable, even in the case of Schumann-Runge bands, the aerosol concentration at two measurement distances must be the same.

When this condition is not fulfilled, it is nevertheless possible to overcome it by using a second spectral line very close to but outside the absorption spectral line considered and emitted following the first one. That also makes it possible to eliminate from the attenuation coefficient $\alpha$ the influence of the oxygen absorption continuum, of the Rayleigh diffusion, of the diffusion of the aerosols and of any residual absorption, particularly that of ozone.

The use of two laser shots slightly offset in frequency complicates a little the practical implementation, but greatly simplifies calculation by avoiding having to image the oxygen absorption continuum, which is not well known (Hertzberg's continuum).

TEMPERATURE MEASUREMENT

Of course, the temperature may be determined by any conventional thermometry method. But already having a density measurement laser available, it is preferable to provide optical measurement of the temperature at a distance by laser excitation.

Let us consider two absorption spectral lines R[E$_0$)J$_0$, E$_1$(J$_1$)] and R'[E'$_0$)J'$_0$, E'$_1$(J'$_1$)] which almost merge, which therefore partially overlap and which belong respectively to two different absorption bands (E$_0$, E$_1$) and (E'$_0$, E'$_1$) whose energy differences between centers E$_1$-E$_0$ and E'$_1$-E'$_0$ closely related, as shown in the diagram of energy levels of FIG. 6.

Roughly, we may write $$\begin{aligned} E_1(J_1) - E_0(J_0) &= E_1'(J_1') - E_0'(J_0') \\ &= h\frac{\omega_0}{2\pi} \\ &= \hbar\,\omega_0 \end{aligned}$$

Let us also consider the fluorescence bands (E$_1$,E$_2$) and (E'$_1$,E'$_2$) such that the probabilities of radiative transition from E$_1$ to E$_2$ and from E'$_1$ to E'$_2$ are high.

Figure 1:
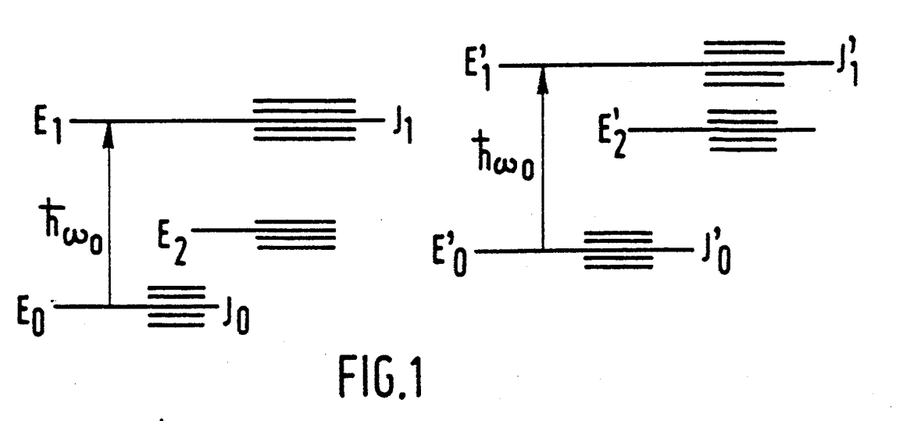
FIG. 1 is a schematic representation of electronic, vibratory and rotatory energy levels of a molecule.
Figure 2:
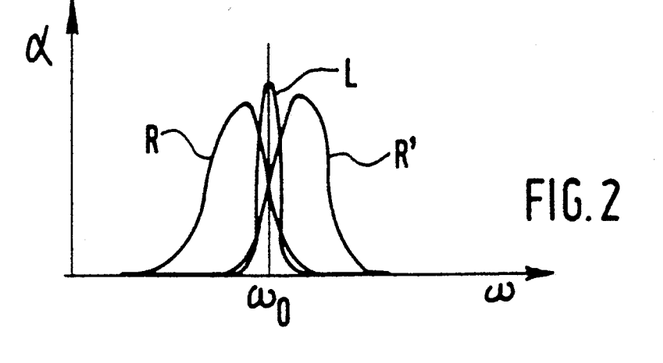
FIG. 2 is a representation of two absorption spectral lines and a laser excitation spectral line.

Let us further consider an excitation radiation L of pulsation $\omega_0$ close to the maxima of the two absorption spectral lines considered R and R', in accordance with the drawing of FIG. 2.

The absorption spectral lines R(R'), as was seen above, have as equation:

$$\alpha(\omega) = N_o S(T) g(\omega)$$

g($\omega$) generally also depending on the temperature T and the pressure P.

The ratio of the fluorescence intensities, i.e. the ratio of the numbers of fluorescence photons received on the two bands, is equal to the ratio of the absorption coefficients $\alpha'/\alpha$ multiplied by the ratio of the fluorescence yields 2'/2. The fluorescence yield is the ratio between the number of molecules whose energy has passed from the high level E$_1$ to the de-excited intermediate level E$_2$ by the spontaneous emission of photons and the total number of molecules excited at the high level E$_1$ by the laser radiation. The fluorescence yields also depend particularly on the temperature T and pressure P.

If we again consider the Schumann-Runge bands, as recalled above, g($\omega$) is practically independent of the temperature and the pressure. Similarly, the fluorescence yields depend no longer on the temperature or the pressure, the pre-dissociation probability being appreciably higher than the transition probability by collision with change of vibratory state.

The ratio of the fluorescence intensities emitted on two bands, resulting from the excitation of the two spectral lines, which are practically merged as mentioned above, by the very fine spectral line laser generator also mentioned above, in the case of two Schumann-Runge bands, therefore only depends on temperature T and is proportional to the ratio of the intensities of the spectral lines $$\frac{S'(T)}{S(T)}$$

The exponential factor of attenuation of the laser beam is strictly eliminated. Since an absorption spectral line is proportional, like the absorption coefficient, to the relative population of the lower level of the transition, the ratio of the fluorescence intensities is therefore substantially equal to $$Ke^{-\frac{E_0'(J_0') - E_0(J_0)}{kT}}$$

k being Boltzmann's constant and K a constant. $E'_0$ and $E_0$ being two different vibratory levels, the energy difference $E'_0 - E_0$ is great with respect to kT, so that this ratio is very sensitive to the temperature. The measurement of this ratio of fluorescence intensities therefore allows the temperature to be calculated.

To sum up, using a laser, particularly an ArF laser, the ambient air can be illuminated over a slice of relatively great depth for exciting, in two different Schumann-Runge bands, two "identical" absorption spectral lines, i.e. almost merging, with respect to which the laser emission spectral line is very fine.

Since it is a question of these particular bands, for which the pre-dissociation probability of the excited state is determinant, the ratio of the absorption coefficients only depends on the temperature and the fluorescence yields are independent of the temperature and the pressure. The ratio of the fluorescence energies (ratio of the numbers of fluorescence photons) in two different bands and resulting from absorption transitions only depends then on the temperature. It is sufficient to measure it to determine this temperature.

Having described the theoretical principles on which the invention is based, the latter will now be described.

MEASUREMENT SYSTEM

Figure 3:
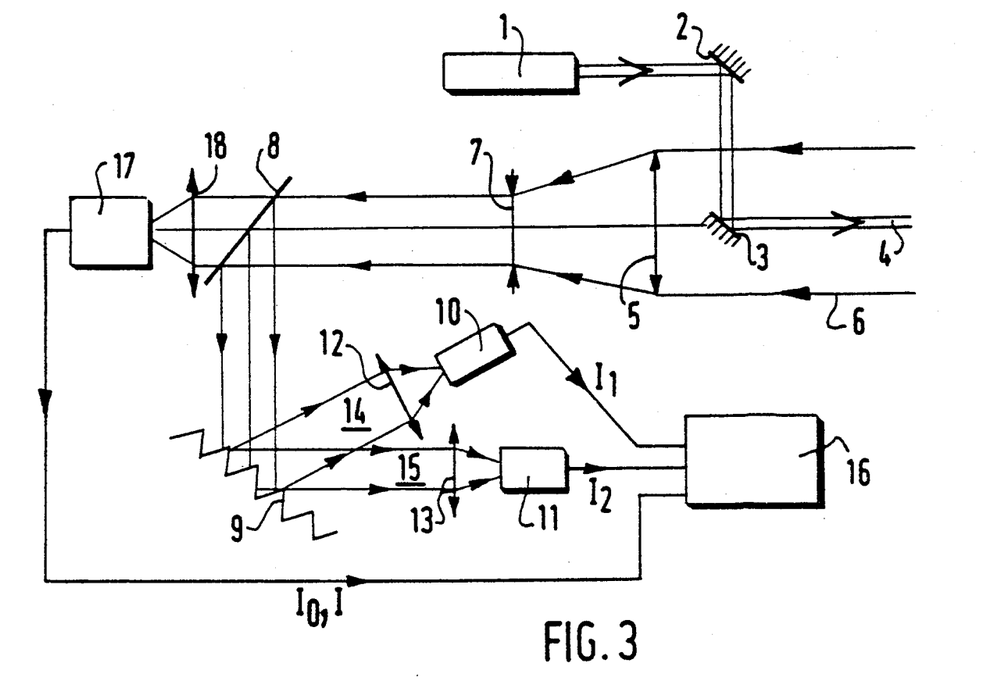
FIG. 3 is the schematic representation of the pressure measurement system of the invention.

The measuring system, shown in FIG. 3, here comprises an excimer ArF laser generator 1 here again of a wavelength substantially equal to 193 nm, emitting into space via two reflection mirrors 2 and 3 an excitation beam 4, a lens 5 for receiving the fluorescence beam 6 resulting from the excitation of the air molecules, a focussing lens 7, in this case a dichroic plate 8 for reflecting the fluorescence beam 6 and for transmitting the backscattered beam, a network 9 on which the beam 6 is reflected at a reflection angle depending on the frequency, for separating these two fluorescence energies 14, 15, two detectors 10, 11 receiving respectively the two fluorescence energies via two focussing lenses 12, 13, a detector 17 receiving the backscattered energy via a focussing lens 18 and a processing and computing module 16.

All the optics are of ultraviolet quality, for example made from UV silica.

Detectors 10, 11, 17 each comprise a photovoltaic effect photomultiplier vacuum tube, as amplifier, and a suitably tuned filter.

MEASUREMENT METHOD

1. Measurement of the Temperature

The lifespan of the excited states $E_1$ and $E'_1$ is very short, less than 10 ps, because of the predissociation. The fluorescence of a given volume consequently only occurs during the passage of a laser pulse of duration $\tau$. Consequently, the measurement volume may be defined in time by the duration of the laser pulse, which advantageously simplifies the optical system.

Figure 4:
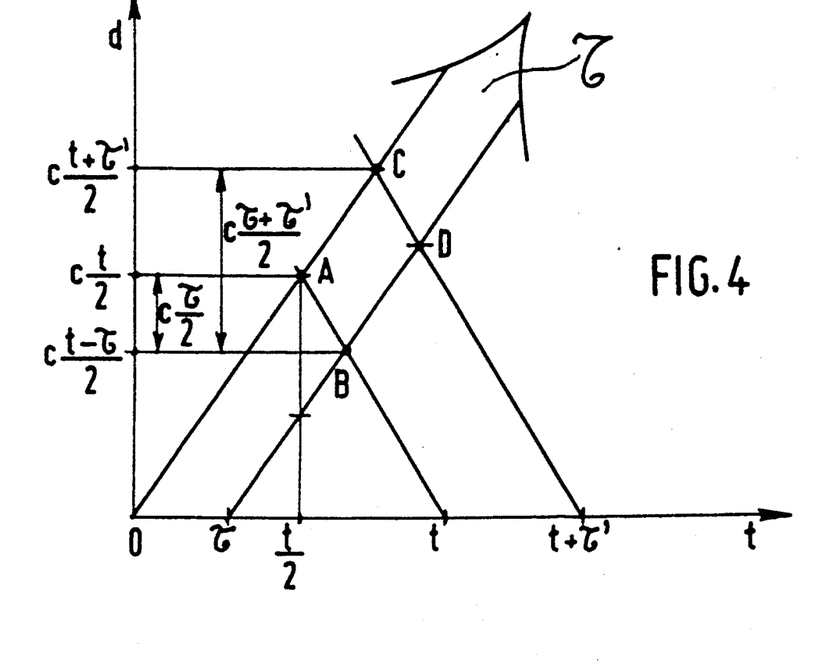
FIG. 4 is a space-time representation of the slice of air sounded, for the temperature.

Transmitter 1 and receivers 10, 11 being practically at the same original position 0, the transmission and fluorescence diagram may be represented as a function of two variables, the measurement or sounding time t and distance d, along the laser beam 4 (FIG. 4). In this figure the space-time trajectory of a laser pulse of duration has been shown.

At each time t, greater than or equal to $\tau$, the fluorescence received comes from a slice in space AB of depth $c\tau/2$, c being the speed of light.

During the analysis time $\tau'$ the instantaneous observation slice moves, at speed c, from AB to CD, i.e. by a distance $c\tau'/2$. The overall observed spatial slice $$\left\{ B\left(c\frac{t-\tau}{2}\right) - C\left(c\frac{t+\tau'}{2}\right) \right\}$$

has a depth of $$c\frac{\tau + \tau'}{2}$$

During this analysis time $\tau'$, the fluorescence energies 14, 15 are measured by detectors 10 and 11 in two different Schumann-Runge bands.

More precisely, the photomultipliers 10, 11 deliver to module 16 two currents $I_1$ and $I_2$ which are integrated during times depending on the sounded air slice and its distance away, before the two integrals are calculated and their ratio determined.

As mentioned above, the ratio $$Ke^{-\frac{E_0' - E_0}{kT}}$$

of the detected signals, stored in module 16, allows the temperature T to be calculated. Naturally, the measurement system will have been calibrated beforehand.

2. Density Measurement

Measurement with two laser spectral lines will be described hereafter.

Figure 7:
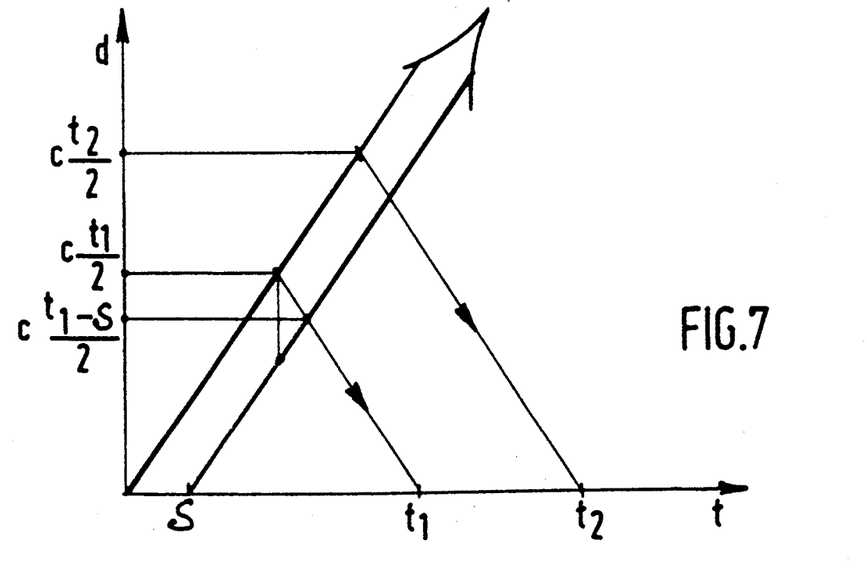
FIG. 7 is another space-time representation of one of the sounded air slices, for the pressure.

FIG. 7 shows the space-time emission and backscatter diagram relative to one of the two laser spectral lines.

Figure 8:
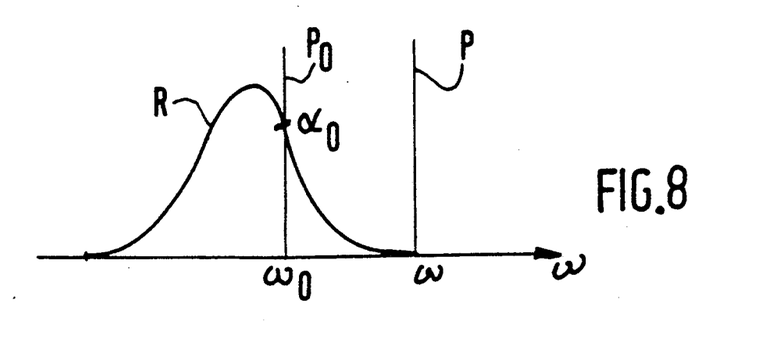
FIG. 8 is a representation of the absorption spectral line for the pressure measurement with two laser spectral lines.

Two laser pulses are emitted successively, one $P_o$ at a frequency $\omega_o$ inside the absorption spectral lines R used for the temperature measurement, the other p, outside, of frequency $\omega$ (FIG. 8). The respective attenuation coefficients of the beam are respectively $\alpha_o$ inside the spectral line, and $\alpha$, outside. $W_o$ and W being thus respectively the backscattered energies for each of the two laser pulses and measured by detector 17, which delivers two currents $I_o$ and I which are integrated during finite times $(t_2 - t_1)$ in module 16, the latter calculates the ratio of the backscattered energies at two times $t_1$ and $t_2$ corresponding to the distances $$D_1 = c\frac{t_1}{2} \text{ and } D_2 = c\frac{t_2}{2}.$$

Module 16 calculates the ratio $$\frac{W_0(D_2)}{W_0(D_1)} \cdot \frac{W(D_1)}{W(D_2)}$$

and $(\alpha_o - \alpha)$ is derived in accordance with the approximate relation $$\frac{W_0(D_2)}{W_0(D_1)} \cdot \frac{W(D_1)}{W(D_2)} \approx e^{-2(\alpha_0 - \alpha)(D_2 - D_1)}$$

Since we may write the relation $$\alpha_0 - \alpha = N_0 \left[ \frac{A}{T} e^{-\frac{E_1}{kT}} + \frac{B}{T} e^{-\frac{E_2}{kT}} \right]$$

in which
  $N_o$ is the molecular density of oxygen,
  T is the temperature, determined elsewhere,
  $E_1$ and $E_2$ are the energies of the lower levels of the two transitions used for the measurement of T,
  A and B are constants,
  module 16 derives $N_o$ therefrom.

PRACTICAL MEASUREMENT CASE

Temperature

It is only given by way of example.

The fluorescence analysis is only carried out after the laser pulse of duration $\tau = 10$ ns, between times $t = 70$ ns and $t + \tau' = 100$ ns ($\tau' = 30$ ns) The sounded air slice extends then between two planes passing through B and C, with reference to FIG. 4, and spaced apart by 9 m and 15 m respectively.

The two integrals are then calculated:

$$T_1 = \int_{t}^{t+\tau'} I_1 dt$$

$$T_2 = \int_{t}^{t+\tau'} I_2 dt$$

From the ratio $$T_1/T_2 = Ke^{-\frac{E_0' - E_0}{kT}}$$

T is derived.

The temperature is in fact determined after each laser pulse.

2. Density

The backscatter analysis is made after each of the two laser pulses. The time intervals $[t_1, t_2]$ and $[t_3, t_4]$ are chosen after each laser pulse, the times being referenced with respect to the beginning of the pulse.

We may for example consider:
  $t_1 = 70$ ns
  $t_2 = 80$ ns
  $t_3 = 100$ ns
  $t_4 = 110$ ns The interval $[t_1, t_2]$ corresponds to a sounded volume extending at a distance between 9 m and 12 m; the interval $[t_3, t_4]$ corresponds to a volume extending between 13.5 m and 16.5 m. Module 16 calculates the integrals $$A_{12}^0 = \int_{t_1}^{t_2} I_0 dt$$

$$A_{34}^0 = \int_{t_3}^{t_4} I_0 dt$$

$$A_{12} = \int_{t_1}^{t_2} I dt$$

$$A_{34} = \int_{t_3}^{t_4} I dt$$

then the ratio $$\frac{A_{34}^0}{A_{12}^0} \cdot \frac{A_{12}}{A_{34}}$$

then, with T known, the oxygen molecular density $N_o$, the dry air molecular density $N_A$ and finally the pressure p, in accordance with the above defined relation. The pressure is in fact also determined after each pair of laser pulses.

CHOICE OF THE PAIR OF ABSORPTION SPECTRAL LINES

Examination of the Schumann-Runge oxygen bands shows that there exist a few pairs of merged absorption spectral lines which may serve for measuring the temperature.

Figure 5:
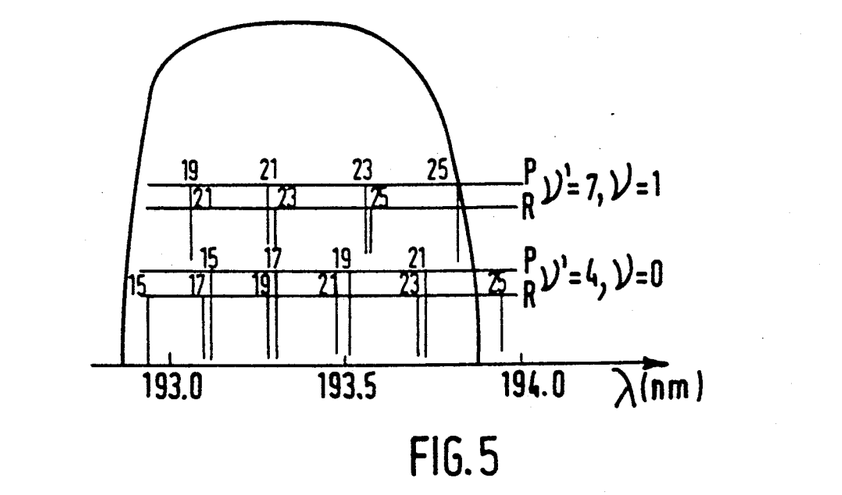
FIG. 5 is a representation of Schumann-Runge bands inn the locking band of the Arf laser.

In the locking band of the Arf laser (FIG. 5), there exist a number of spectral lines belonging particularly to two bands $[X_0, B_4]$
  $[X_1, B_7]$ the indices 0, 1, 4, 7 of the electronic states X, B representing vibratory level numbers (vibrational quantal number) associated with these electronic states. It is a question of the spectral lines
  P17 of band $X_0, B_4$
  R23 of band $X_1, B_7$
and
  R19 of band $X_0, B_4$
  P21 of band $X_1, B_7$ P and R, in the bands considered, correspond to the branches in which the difference between the orbital moments of the two states B and X is equal to $-1$ and $+1$ respectively.

The spectral lines of the first pair are merged to better than 0.1 cm$^{-1}$ and those of the second pair are only separated by about 2 cm$^{-1}$.

The spectral line width, due to pre-dissociation is about 3.4 cm$^{-1}$ for the band $[X_0, B_4]$ and 1.4 cm$^{-1}$ for the band $[X_1, B_7]$: the spectral lines considered indeed overlap.

The choice of the pair of spectral lines must be determined by the sounding distance in order to optimize the signal/noise ratio. For a distance of about 10 m, the absorption coefficient of the spectral lines of the band $[X_0,B_4]$ is too high for a pressure of 1 bar and it is then advisable to choose the pair of spectral lines offset by 2 $cm^{-1}$ and adjust the frequency of the laser to the center of the spectral line of the band $[X_1,B_7]$.

FLUORESCENCE BANDS

The fluorescence bands [B,X] from levels $B_4$ and $B_7$ must be both intense and weakly absorbed. Furthermore, the fluorescence wavelengths must be chosen greater than 240 nm so as to be outside the Herzberg oxygen continuum (Herzberg continuum cross section of oxygen, Cheung et al., Canadian Journal of Physics, vol 62, pages 1752-1762, 1984).

All the interesting fluorescence bands fall however in Hartley's band of ozone which forms an absorption continuum extending to 360 nm. The absorption maximum occurs at 255 nm and the ozone concentration is maximum at an altitude of about 20 km with an absorption coefficient $\alpha max = 5.10^{-3} m^{-1}$. It has been observed that two intense fluorescence bands, among others, close to the absorption maximum of ozone, were in particular usable. These are the bands $[B_4,X_8]$
$[B_7,X_9]$ having respective wavelengths of 249 nm and 247 nm.

In the system of the invention such as described with reference to FIG. 3, the detectors 10,11 are tuned to the corresponding frequencies which are separated by the network 9. Since the absorption deviation of ozone is small, its influence on the ratio of the transmitted fluorescence energies is negligible between 0 and 30 km of altitude. In fact, it can be readily demonstrated that if the maximum deviation of the absorption coefficient is $5.10^{-4} m^{-1}$, the relative maximum variation of the transmission ratio is $5.10^{-3}$ for a distance of 10 m. To such a variation there corresponds a relative temperature variation ten times smaller. For a temperature of 300 K, the maximum temperature variation is therefore 0.15 K.

It should be noted that the performances of the measurement method and system of the invention are limited by the detection photon noise. But, for example, with the measurement distances considered above, a laser pulse energy of 0.01 J, an optical reception area of 100 $cm^2$ and an average of measurements made over 10 shots, between 0 and 20 km in altitude, the effective computing uncertainties due to photon noise are less than 0.5K for the temperature and 0.7% for the oxygen density.

The measurement method which has just been described was based on a pair of absorption spectral lines in the locking band of the ArF laser.

The Applicant has sought, outside the band of this laser, all the pairs of merged spectral lines which can be used over two bands $[X_{v1}, B_{v'1}]$ and $[X_{v2},B_{v'2}]$.

The vibrational quantal numbers v and $v_2$ of the fundamental state must be equal to 0 or 1, so that the population of the corresponding states and so the absorption are sufficient. The number $v'_1$ has been limited to 4, for the spectral lines of the bands $[X_0,B_{v'>4}]$ are too absorbent for a distance of 10 m. The values of v' equal to 0 and 2 have been eliminated for, for them, the rate of pre-dissociation is not high enough for the profile of the spectral line to be independent of the pressure. With these restrictions posed, two other merging spectral lines have been found. These are the spectral line R25 of band $X_0,B_3$
P9 of band $X_1,B_5$ at a wavelength $\tau = 196.2$ nm, R21 of band $X_0,B_1$
R5 of band $X_1,B_3$ at a wavelength $\tau = 200.9$ nm, the latter pair being however less interesting for the absorption coefficients are low. For the first pair an alexandrite laser could be used after multiplication of the frequency by 4. In this latter case, the fluorescence bands from levels $B_3$, $B_5$ which could be used would be $[B_3,X_8]$ and $[B_5,X_{10}]$.

What is claimed is:

1. A method for optical remote measurement of the pressure of the air by laser excitation in which, having determined the air temperature, backscattered radiation is caused by means of a laser generator with very fine spectral line and by excitation of an absorption spectral line of molecular oxygen, the backscattered energies are measured at two different distances, the ratio of these energies is determined, a coefficient of absorption is derived therefrom depending on the temperature and the molecular density of oxygen and the density and so the pressure is calculated, wherein an absorption spectral line is excited belonging to a Schumann-Runge band of molecular oxygen and the absorption spectral line is very wide with respect to the Rayleigh diffusion spectrum.

2. The measurement method as claimed in claim 1, wherein the laser generator emits two successive emission spectral lines which are very fine with respect to the absorption spectral line and are offset in frequency.

3. The measurement method as claimed in claim 2, wherein one of the laser emission spectral lines is inside the absorption spectral line, the other outside.

4. The measurement method as claimed in claim 1, wherein the pressure is calculated after each laser pulse.

5. The measurement method as claimed in claim 1, wherein, to determine the temperature, an optical measurement is made at a distance and, by means of the laser generator, two absorption spectral lines are excited which at least overlap and which belong respectively to two different Schumann-Runge bands of molecular oxygen, the emission spectral line of the laser generator has a very small width with respect to that of the absorption spectral lines and its central frequency is adjusted to be close to the maxima of the two absorption spectral lines, fluorescence of the oxygen is caused, the intensities of fluorescence induced in two different bands are measured, the ratio of these intensities is determined and the temperature derived therefrom.

6. The measurement method as claimed in claim 1, wherein at least one of the Schumann-Runge bands is excited having a vibrational quantal number of the fundamental state 0 or 1.

7. The measurement method as claimed in claim 6, wherein an ArF laser is used and at least one of the two bands $[X_0,B_4]$ and $[X_1,B_7]$ is excited.

8. The measurement method as claimed in claim 7, wherein at least one of the two spectral lines P17 of the band $[X_0,B_4]$ and R23 of the band $[X_1,B_7]$ is excited.

9. The measurement method as claimed in claim 7, wherein at least one of the two spectral lines R19 of the band $[X_0,B_4]$ and P21 of the band $[X_1,B_7]$ is excited.

10. The measurement method as claimed in claim 9, wherein the frequency of the generator is adjusted to the center of the spectral line P21 of the $[X_1,B_7]$.

11. The measurement method as claimed in claim 6, wherein at least one of the absorption spectral lines R25 of band $[X_0,B_3]$ and R9 of band $[X_1,B_5]$ is excited.

12. The measurement method as claimed in claim 1, wherein the temperature and the pressure of the air is determined in front of an aircraft in a slice of air free of aerodynamic disturbances and flight parameters of the aircraft are derived therefrom which are used for piloting same.

13. A measurement system for implementing the method as claimed in claim 1, comprising a laser generator emitting radiation with a very fine spectral line, an optical system emitting the excitation radiation, an optical system receiving the fluorescence and backscattered radiation, means for separating the backscattered radiation and the fluorescence radiation, a detector for receiving the backscattered radiation, means for separating the two fluorescence energies, detectors tuned respectively to the fluorescence frequencies and a processing and computing module.

14. The system as claimed in claim 13, wherein the laser generator is an ArF excimer laser generator emitting at least a monochromatic parallel beam with very fine spectral line centered on a wavelength substantially equal to 193 nm.

* * * * *